(12) United States Patent
Morgan, III et al.

(10) Patent No.: US 9,499,770 B2
(45) Date of Patent: Nov. 22, 2016

(54) FRESHENING COMPOSITIONS RESISTING SCENT HABITUATION

(71) Applicant: The Procter & Gamble Company, Cincinnati, OH (US)

(72) Inventors: George Kavin Morgan, III, Hamilton, OH (US); Jonathan Robert Cetti, Mason, OH (US); Zerlina Guzdar Dubois, Mason, OH (US); Virginia Tzung-Hwei Hutchins, Cincinnati, OH (US); Michael Wayne Kinsey, Lebanon, OH (US); Michael-Vincent Nario Malanyaon, Indian Springs, OH (US); Jennifer Lea Rinker, Fairfield, OH (US); Ronald David Turner, Walton, KY (US); Christine Marie Readnour, Ft. Mitchell, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/642,913

(22) Filed: Mar. 10, 2015

(65) Prior Publication Data

US 2016/0264909 A1    Sep. 15, 2016

(51) Int. Cl.
*A61K 8/18* (2006.01)
*A61Q 13/00* (2006.01)
*C11B 9/00* (2006.01)
*A61L 9/00* (2006.01)

(52) U.S. Cl.
CPC ............... *C11B 9/0011* (2013.01); *A61L 9/00* (2013.01); *A61Q 13/00* (2013.01); *C11B 9/003* (2013.01); *C11B 9/0034* (2013.01); *C11B 9/0076* (2013.01); *C11B 9/0084* (2013.01); *C11B 9/0092* (2013.01); *C11B 9/0096* (2013.01)

(58) Field of Classification Search
CPC ..... C11B 9/011; C11B 9/003; C11B 9/0034; C11B 9/0076; C11B 9/0096
USPC .......................................................... 512/7
See application file for complete search history.

(56) References Cited

U.S. PATENT DOCUMENTS

| | | | |
|---|---|---|---|
| 3,928,248 A | 12/1975 | Mookherjee et al. | |
| 4,324,703 A | 4/1982 | Seldner | |
| 4,430,243 A | 2/1984 | Bragg | |
| 5,538,719 A | 7/1996 | Preti et al. | |
| 5,574,179 A | 11/1996 | Wahl et al. | |
| 5,576,282 A | 11/1996 | Miracle et al. | |
| 5,597,936 A | 1/1997 | Perkins et al. | |
| 5,651,976 A | 7/1997 | Price et al. | |
| 5,861,144 A | 1/1999 | Peterson et al. | |
| 6,103,678 A | 8/2000 | Masschelein et al. | |
| 6,150,409 A | 11/2000 | Restrepo et al. | |
| 6,225,464 B1 | 5/2001 | Hiler, II et al. | |
| 6,326,348 B1 | 12/2001 | Vinson et al. | |
| 6,413,920 B1 | 7/2002 | Bettiol et al. | |
| 6,458,754 B1 | 10/2002 | Velazquez et al. | |
| 6,488,943 B1 | 12/2002 | Beerse et al. | |
| 6,531,444 B1 | 3/2003 | Shefer et al. | |
| 7,018,978 B2 | 3/2006 | Miracle et al. | |
| 7,119,060 B2 | 10/2006 | Shefer et al. | |
| 7,223,361 B2 | 5/2007 | Kvietok et al. | |
| 7,316,994 B2 | 1/2008 | Jordan, IV et al. | |
| 7,365,043 B2 | 4/2008 | Baker et al. | |
| 7,585,833 B2 | 9/2009 | Fadel et al. | |
| 7,590,232 B2 | 9/2009 | Carter et al. | |
| 7,722,807 B2 | 5/2010 | Keller, Jr. et al. | |
| 7,763,238 B2 | 7/2010 | Preti et al. | |
| 8,603,963 B1 | 12/2013 | Steward et al. | |
| 8,651,395 B2 | 2/2014 | Kvietok et al. | |
| 2004/0110898 A1 | 6/2004 | Dreja et al. | |
| 2004/0156742 A1 | 8/2004 | Milan et al. | |
| 2005/0143282 A1 | 6/2005 | Creutz et al. | |
| 2006/0003913 A1 | 1/2006 | Boutique et al. | |
| 2006/0263313 A1 | 11/2006 | Scavone et al. | |
| 2007/0275866 A1 | 11/2007 | Dykstra | |
| 2008/0138441 A1 | 6/2008 | Schwartz et al. | |
| 2009/0324660 A1 | 12/2009 | Cetti et al. | |
| 2010/0028288 A1 | 2/2010 | Tranzeat et al. | |
| 2010/0308130 A1 | 12/2010 | Gruenbacher et al. | |
| 2012/0121677 A1 | 5/2012 | Franklin | |
| 2014/0170101 A1 | 6/2014 | Cetti et al. | |
| 2014/0170102 A1 | 6/2014 | Cetti et al. | |
| 2014/0170194 A1* | 6/2014 | Cetti | A61K 8/46 424/401 |
| 2014/0179722 A1 | 6/2014 | Cetti et al. | |
| 2014/0179748 A1 | 6/2014 | Cetti et al. | |

FOREIGN PATENT DOCUMENTS

| | | |
|---|---|---|
| JP | 2005-170811 A | 6/2005 |
| WO | WO 2008/149065 A1 | 12/2008 |
| WO | WO 2010/094546 A3 | 8/2010 |

OTHER PUBLICATIONS

Iranshahi, (The Journal of Essential Oil Research, Aug. 2012, vol. 24, pp. 393-434).
Goodscents company—dibutyl sulfide, (http://www.thegoodscentscompany.com/data/rw1 018851.html, dibutyl sulfide, 2015).

(Continued)

*Primary Examiner* — Ling Choi
*Assistant Examiner* — Jessica E Whiteley
(74) *Attorney, Agent, or Firm* — Abbey A. Lopez; Amy I. Ahn-Roll

(57) ABSTRACT

The present application relates to perfume raw materials, perfume blends, perfume delivery systems and air care products comprising such perfume raw materials, perfume blends and/or such perfume delivery systems, as well as processes for making and using such perfume raw materials, perfume delivery systems and air care products. The perfume blends disclosed herein expand the perfume communities' options.

42 Claims, No Drawings

(56) References Cited

OTHER PUBLICATIONS

Del Valle, Process Biochemistry, 2003, pp. 1-14.
Fortineau (Journal of Chemical Education, 2004, vol. 81, pp. 45-50).
"The nature and duration of adaptation following long-term odor exposure", Perception & Psychophysics 1996, 58(5), 781-792.
PCT International Search Report and Written Opinon for PCT/US2013/074986 dated May 19, 2014.
Standard Practice for Determination of Odor and Taste Thresholds by a Forced-Choice Ascending Concentration Series Method of Limits, ASTM International, Designation: E679-04 (Reapproved 2011), pp. 1-7.
U.S. Appl. No. 14/705,373, filed May 6, 2015, Lynette Anne Makins Holland.
All Office Actions, U.S. Appl. No. 14/105,230.

* cited by examiner

US 9,499,770 B2

FRESHENING COMPOSITIONS RESISTING SCENT HABITUATION

FIELD OF INVENTION

The present application relates to freshening compositions comprising perfume blends and sulfur-containing perfume raw materials that resist scent habituation, as well as processes for making and using such compositions to resist consumer scent habituation.

BACKGROUND OF THE INVENTION

Air care products may comprise freshening compositions having one or more perfume raw materials ("PRMs", or individually "PRM") that can provide a desired scent to such product and/or a situs that is contacted with such a product and/or mask an undesirable odor. While current PRMs provide desirable odors, consumers continue to seek products that have scents that may be longer lasting and that are tailored to their individual desires—unfortunately consumers become habituated to the scent provided but the PRMs and perfume blends continue to be volatilized from the air care product. As a result, ever increasing amounts of such PRMs and/or perfume blends are required to achieve the same effect or the consumer must switch to a different product and/or perfume for a significant period of time to reverse such habituation.

To address habituation, perfumers have formulated perfume blends with PRMs that are believed to provide anti-habituating benefits. Surprisingly, Applicants found that certain sulfur-containing PRMs are superior in anti-habituating benefits when used in freshening compositions. Therefore, Applicants identified freshening compositions comprising such PRMs, perfume blends and/or such perfume delivery systems, as well as processes for making and using such freshening compositions that are not as susceptible to habituation.

SUMMARY OF THE INVENTION

The present application relates to freshening compositions comprising perfume blends and sulfur-containing PRMs resisting scent habituation and air care products comprising such freshening compositions, as well as processes for making and using such freshening compositions and air care products.

A freshening composition is provided comprising a perfume blend comprising about 0.0000001% to about 10%, by weight of said perfume blend, of a sulfur accord, said sulfur accord comprises: (a) about 1% to about 99%, by weight of said sulfur accord, of 1-butylsulfanylbutane; and (b) about 1% to about 99%, by weight of said sulfur accord, of a sulfur-containing perfume raw material selected from the group consisting of: 2-(4-methyl-1,3-thiazol-5-yl)ethanol; 2-methylthio-3-methyl sulfanyl pryazine; 5-Mercapto-5-methyl-3-hexanone; 4,7,7-trimethyl-6-thiabicyclo[3.2.1]octane; 2-isobutylthiazole; 2-isopropyl-4-methyl thiazole; 5-methyl-2-(2-sulfanylpropan-2-yl)cyclohexan-1-one; limonene thiol; 4 methyl 4 mercapto pentane 2 one 1 ppm TEC; 2-acetyl thiazole; oxane; 4-methoxy-2-methyl-2-butanethiol; 4,7,7-trimethyl-6-thiabicyclo[3.2.1]octane; and mixtures thereof; wherein said composition resists the fragrance habituation of a consumer to the freshening composition.

Also provided is a freshening composition comprising a perfume blend, said perfume blend comprising about 0.0000001% to about 10%, by weight of said perfume blend, of a sulfur accord, said sulfur accord comprises from about 0.003% to about 0.01%, by weight of said composition, of 1-butylsulfanylbutane, 5-mercapto-5-methyl-3-hexanone, and 4,7,7-trimethyl-6-thiabicyclo[3.2.1]octane.

Also provided is a method of reducing fragrance habituation comprising providing the compositions disclosed herein.

DETAILED DESCRIPTION OF THE INVENTION

Definitions

As used herein, "air care product" means products for treating or fragrancing the air including energized (i.e. electrically powered) air freshening delivery systems including fan-based diffusers, liquid electric pluggable air fresheners, electromechanical actuating diffusers; passive diffusers (i.e. not electrically powered) including membrane-based in-room air fresheners, car vent air fresheners As used herein, articles such as "a" and "an" when used in a claim, are understood to mean one or more of what is claimed or described.

As used herein, "freshening composition" means a composition that includes one or more perfume raw materials that is intended to treat (e.g. eliminate or reduce/minimize malodors), fragrance, and/or freshen the air. The freshening composition may be used with or without an air care product. Freshening compositions of the present invention include PRMs and may additionally include water, solubilizers, surfactants, diluents, malodor reducing actives, and perfume materials.

As used herein, "habituating" refers an individual or group who has decreased sensitivity to perceiving a fragrance or fragrance material. A fragrance or fragrance material is considered habituating when their Degree of Habituation (percent change in the odor dectection threshold) is greater than 150%, greater than 300%, greater than 500%, greater than 1000% according to the method described in the Test Methods section of this specification.

As used herein, "include", "includes" and "including" are meant to be non-limiting.

As used herein, "sulfur accord" means a mixture of sulfur-containing perfume raw materials. All perfume raw materials that lack a sulfur atom may be considered part of the perfume blend and/or the total freshening composition, but such perfume raw materials would not be part of the sulfur accord.

The perfume raw materials ("PRMs") disclosed, claimed and/or used in the perfume blends claimed and/or described herein encompass any stereoisomers of such PRMs.

Unless otherwise noted, all component or composition levels are in reference to the active portion of that component or composition, and are exclusive of impurities, for example, residual solvents or by-products, which may be present in commercially available sources of such components or compositions.

Freshening Compositions

Freshening compositions can come in a variety of forms. For example, a freshening composition can be in a liquid form and can be a sprayable fabric refresher and/or air freshener; a diffusive air freshener such as the liquid compositions used in FEBREZE® NOTICEables™ air freshener, FEBREZE Car Vent™ air freshener, or FEBREZE Set & Refresh™ air freshener. Freshening compositions can also be in a solid or gel form. Many consumers prefer freshening compositions that can consistently provide a desired scent that can be perceived each time the composition or product is used. These perfume (i.e., fragrance) materials can include perfume blends, perfume accords, PRMs, and perfume delivery systems. Habituation of the perfume materials by the consumer, however, can lead to a diminished perception of the desired scent even when the quantity of a PRM in the freshening composition remains consistent.

Freshening compositions can resist scent habitation by incorporating a perfume blend containing a sulfur accord. The sulfur accord can help the freshening composition resist consumer scent habituation.

Perfume Blend Containing a Sulfur Accord

The perfume blend of the present composition comprises a sulfur accord having a mixture of sulfur-containing PRMs. Non-limiting examples of compounds that have a sulfur or sulfide moiety can include 1-butylsulfanylbutane (or dibutylsulfide); ethyl 3-methylsulfanylpropanoate; 2-(methylsulfanylmethyl)furan; methylsulfanylmethane; methylsulfanylethane; 3-methylsulfanylprop-1-ene; S-methyl ethanethioate; ethylsulfanylethane; 1-methylsulfanylpropane; S-ethyl ethanethioate; 1-methylsulfanylbutane; 2-propan-2-ylsulfanylpropane; bis(methylsulfanyl)methane; 1-ethylsulfanylpropane; thiolane; 1-propylsulfanylpropane; 1-ethylsulfanylbutane; S-ethyl propanethioate; S-methyl butanethioate; S-methyl 3-methylbutanethioate; 3-methylsulfanylpropanal; 3-prop-2-enylsulfanylprop-1-ene; methyl 2-methylsulfanylacetate; S-prop-2-enyl propanethioate; 1-methylsulfanylbutan-2-one; 4-methylsulfanylbutan-2-one; 3-methylsulfanylpropan-1-am; 2,4,6-trimethyl-1,3,5-trithiane; 3-methylsulfanylbutanal; 2-methyl-1,3-thiazolidine; 2-methyl-4,5-dihydro-1,3-thiazole; ethyl 2-methylsulfanylacetate; methyl 3-methylsulfanylpropanoate; S-propan-2-yl 3-methylbutanethioate; 4-methyl-4-methylsulfanylpentan-2-one; 2-methyl-1,3-dithiolane; methyl 2-methylsulfanylbutanoate; S-methyl furan-2-carbothioate; S-propan-2-yl 3-methylbut-2-enethioate; thiolan-3-one; 3,5-diethyl-1,2,4-trithiolane; methylsulfanylmethylbenzene; 3-methylsulfanylpropan-1-ol; 2-(propan-2-ylsulfanylmethyl)furan; 2-methyl-5-methylsulfanylfuran; S-(furan-2-ylmethyl) methanethioate; 1,2,4-trithiolane; 2-methylthiolan-3-one; 4-methylsulfanylbutan-1-ol; S-butan-2-yl 3-methylbutanethioate; S-butan-2-yl 3-methylbut-2-enethioate; S-(furan-2-ylmethyl) ethanethioate; 2-propyl-1,3-thiazolidine; 3-methyl-1,1-bis(methylsulfanyl)butane; 3-ethylsulfanylpropan-1-ol; S-methyl benzenecarbothioate; 3,5-dimethyl-1,2,4-trithiolane; S-butan-2-yl 2-methylbutanethioate; methylsulfanylbenzene; 1-pentylsulfanylpentane; (2R,4S)-2-methyl-4-propyl-1,3-oxathiane; 2-methyl-4-propyl-1,3-oxathiane; ethyl 2-methyl-2-methylsulfanylpropanoate; S-(furan-2-ylmethyl) propanethioate; 4,7,7-trimethyl-6-thiabicyclo[3.2.1]octane; 3-methyl-1,2,4-trithiane; methylsulfanylmethyl hexanoate; 1-(4,5-dihydro-1,3-thiazol-2-yl)ethanone; 3-methylsulfanylpropanoic acid; 5-methylsulfanyl-2-(methylsulfanylmethyl)pent-2-enal; 4,5-dimethyl-2-(2-methylpropyl)-2,5-dihydro-1,3-thiazole; 3-methylsulfanylhexan-1-ol; 2-methyl-4,5-dihydrofuran-3-thiol acetate; 4-(3-oxobutylsulfanyl)butan-2-one; 3-methylsulfanylbutanoic acid; 2-methylsulfanylpyrazine; 2-methyl-3-methylsulfanylpyrazine; 2-(furan-2-ylmethylsulfanylmethyl)furan; 2-(methylsulfanylmethyl)pyrazine; 3,5-di(propan-2-yl)-1,2,4-trithiolane; 2-methylsulfanylphenol; 2-methyl-3-methylsulfanylpyrazine; ethyl 3-(furan-2-ylmethylsulfanyl)propanoate; 2,2,4,4,6,6-hexamethyl-1,3,5-trithiane; 2-methyl-5,7-dihydrothieno[3,4-d]pyrimidine; 2-amino-4-methylsulfanylbutanoic acid; (2S)-2-amino-4-methylsulfanylbutanoic acid; 2',3a-dimethylspiro[6,6a-dihydro-5H-[1,3]dithiolo[4,5-b]furan-2,3'-oxolane]; 2,5-dimethyl-1,4-dithiane-2,5-diol; methyl 2-thiofuroate; and mixtures thereof.

More specific examples of sulfur-containing PRMs that have a sulfur or sulfide moiety can include PRMs listed in Table 1.

TABLE 1

| PRM Chemical Name |
| --- |
| 1-butylsulfanylbutane |
| 2-(4-methyl-1,3-thiazol-5-yl)ethanol |
| 5-Mercapto-5-methyl-3-hexanone |
| 4,7,7-trimethyl-6-thiabicyclo[3.2.1]octane |
| 2-(2-methylpropyl)-1,3-thiazole |
| 4-methyl-2-propan-2-yl-1,3-thiazole |
| 5-methyl-2-(2-sulfanylpropan-2-yl)cyclohexan-1-one |
| 6-Thiabicyclo[3.2.1]octane |
| 4-methyl-4-sulfanylpentan-2-one |
| 8-Mercaptomenthone (CAS #38462-22-5) |
| (2R,4S)-2-methyl-4-propyl-1,3-oxathiane (CAS #59323-76-1) |

More specific examples of compounds that have a sulfide moiety can include ethyl 3-methylsulfanylpropanoate; and 2-(methylsulfanylmethyl)furan.

The sulfur accord may comprise a mixture of sulfur-containing PRMs comprising 1-butylsulfanylbutane; 5-Mercapto-5-methyl-3-hexanone; and 4,7,7-trimethyl-6-thiabicyclo[3.2.1]octane.

The perfume blend may also include compounds containing oxygen, sulfur, and nitrogen including 2-(4-methyl-1,3-thiazol-5-yl)ethanol; 1-(1,3-thiazol-2-yl)ethanone; 6-methyl-7-Oxa-1-thia-4-azaspiro[4,4]nonane; 2-[(furan-2-ylmethyl)sulfanyl]-5-methylpyrazine; 2,4-Dimethyl-5-acetylthiazole; 2-ethoxy-1,3-thiazole; 5-methoxy-2-methyl-1,3-thiazole; 1-(4,5-dihydro-1,3-thiazol-2-yl)ethanone; 1-(1,3-thiazol-2-yl)propan-1-one; 1-(2,4-dimethyl-1,3-thiazol-5-yl)ethanone; 2-amino-4-methylsulfanylbutanoic acid; (2S)-2-amino-4-methylsulfanylbutanoic acid; 8-Hydroxy-5-quinolinesulfonic acid; 2-aminoethanesulfonic acid; 2-phenyl-3H-benzimidazole-5-sulfonic acid. More specific examples of a compound comprising oxygen, sulfur, and nitrogen can include 2-(4-methyl-1,3-thiazol-5-yl)ethanol, 1-(1,3-thiazol-2-yl)ethanone; and 6-methyl-7-Oxa-1-thia-4-azaspiro[4,4]nonane.

In one aspect, any of said PRMs disclosed herein may be present in a perfume blend at a level below their respective odor detection thresholds. For example, the perfume blends and freshening compositions comprising same may comprise one or more, for example 1, 2, 3, 4, 5, 6, 7, 8, 9, or 10 etc., of the anti-habituating sulfur-containing PRMs at levels below the respective odor detection thresholds of such anti-habituating sulfur-containing PRMs.

A non-limiting example of an anti-habituation sulfur accord suitable for incorporation into a perfume blend of the present invention is disclosed in Table 2.

TABLE 2

| PRMs | wt % in perfume blend | wt % in sulfur accord |
|---|---|---|
| 1-butylsulfanylbutane | 0.003 | 1.010 |
| Sauvignone 100 | 0.174 | 58.586 |
| 4,7,7-trimethyl-6-thiabicyclo[3.2.1]octane | 0.120 | 40.404 |
| TOTAL | 0.297 | 100.000 |

Suitable sulfur-containing PRMs may be obtained from: Fisher Scientific, 2000 Park Lane Dr., Pittsburgh, Pa. 15275, United States; Symrise GmbH, Muhlenfeldstrasse 1, Holzminden, 37603, Germany; International Flavors & Fragrances Inc., 521 W 57th Street, New York, N.Y. 10019, United States; Givaudan Suisse SA, 1214 Vernier, Switzerland; Firmenich Inc., 250 Plainsboro Rd., Plainsboro Township, N.J. 08536, United States; and Takasago International Corporation (U.S.A.), 4 Volvo Drive, Rockleigh, N.J. 07647, United States.

The sulfur accord of the present invention may be formulated into a perfume blend in an amount from about 0.0000001% to about 10%, or from about 0.0000001% to about 5%, or from about 0.000005% to about 2.5%, or from about 0.00001% to about 1%, or from about 0.000025% to about 0.5%, or from about 0.001% to about 0.5%, or from about 0.003% to about 0.1%, by weight of said freshening composition. The freshening composition may comprise, based on total weight, from about 0.0001% to about 100% of the perfume blend comprising a sulfur accord. Table 3 shows an exemplary perfume blend comprising a sulfur accord or mixture of sulfur-containing PRMs. The perfume blend of Table 3 may be formulated in a freshening composition at 100 wt % or the balance of composition may comprise known adjunct ingredients for freshening compositions, and/or a perfume delivery system.

TABLE 3

| # | CAS Number | Raw Material Name | Wt % |
|---|---|---|---|
| 1 | | 2 6 Nonadienol 10% in dipropylene glycol | 0.249 |
| 2 | 67634-00-8 | Allyl Amyl Glycolate | 0.099 |
| 3 | 2705-87-5 | Allyl Cyclohexane Propionate | 0.994 |
| 4 | 142-19-8 | Allyl Heptoate | 0.994 |
| 5 | 123-11-5 | Anisic Aldehyde | 0.298 |
| 6 | 100-52-7 | Benzaldehyde | 0.149 |
| 7 | 119-53-9 | Benzoin Synthetic No. 63 PF Mod 1 | 0.646 |
| 8 | 140-11-4 | Benzyl Acetate | 14.910 |
| 9 | 928-96-1 | Beta Gamma Hexenol | 0.298 |
| 10 | 33704-61-9 | Cashmeran | 0.099 |
| 11 | 104-54-1 | Cinnamic Alcohol | 0.050 |
| 12 | 3681-71-8 | Cis 3 Hexenyl Acetate | 0.447 |
| 13 | 65405-77-8 | Cis-3-Hexenyl Salicylate | 0.497 |
| 14 | 35854-86-5 | Cis-6-Nonen-1-OL FCC | 0.060 |
| 15 | 5392-40-5 | Citral | 0.249 |
| 16 | 106-22-9 | Citronellol | 0.298 |
| 17 | 150-84-5 | Citronellyl Acetate | 0.099 |
| 18 | 7492-67-3 | Citronellyl Oxyacetaldehyde | 0.050 |
| 19 | 68901-15-5 | Cyclo Galbanate | 0.099 |
| 20 | 103-95-7 | Cymal | 1.093 |
| 21 | 57378-68-4 | Delta Damascone | 0.646 |
| 22 | 63314-79-4 | Delta Muscenone | 0.149 |
| 23 | 18479-58-8 | Dihydro Myrcenol | 12.226 |
| 24 | 58985-18-5 | Dihydro Terpinyl Acetate | 0.497 |
| 25 | 151-05-3 | Dimethyl Benzyl Carbinyl Acetate | 0.199 |
| 26 | 10094-34-5 | Dimethyl Benzyl Carbinyl Butyrate | 0.298 |
| 27 | 34590-94-8 | Dipropylene Glycol Methyl Ether | 9.135 |
| 28 | 39255-32-8 | Ethyl 2 Methyl Pentanoate | 0.646 |
| 29 | 141-97-9 | Ethyl Acetoacetate | 2.485 |
| 30 | 77-83-8 | Ethyl Methyl Phenyl Glycidate | 0.298 |
| 31 | 121-32-4 | Ethyl Vanillin | 0.199 |
| 32 | 7452-79-1 | Ethyl-2-Methyl Butyrate | 0.298 |
| 33 | 105-95-3 | Ethylene Brassylate | 1.491 |
| 34 | 67634-15-5 | Floralozone | 0.298 |
| 35 | 80623-07-0 | Fruitate | 0.994 |
| 36 | 706-14-9 | Gamma Decalactone | 0.994 |
| 37 | 104-50-7 | Gamma Octalactone FCC | 1.093 |
| 38 | 105-87-3 | Geranyl Acetate | 0.199 |
| 39 | 24851-98-7 | Hedione Hc | 0.497 |
| 40 | 1205-17-0 | Helional | 0.398 |
| 41 | 141773-73-1 | Helvetolide | 1.491 |
| 42 | 142-92-7 | Hexyl Acetate | 2.584 |
| 43 | 107-75-5 | Hydroxycitronellal | 1.789 |
| 44 | 68908-82-7 | Indolene | 0.199 |
| 45 | 127-41-3 | Ionone Alpha | 0.497 |
| 46 | 14901-07-6 | Ionone Beta | 0.497 |
| 47 | 127-51-5 | Ionone Gamma Methyl | 0.497 |
| 48 | 58430-94-7 | Iso Nonyl Acetate | 8.449 |
| 49 | 32764-98-0 | Jasmolactone | 0.020 |
| 50 | 198404-98-7 | Javanol | 0.099 |
| 51 | 81786-73-4 | Koavone | 2.982 |
| 52 | 67633-96-9 | Liffarome | 0.646 |
| 53 | 68039-49-6 | Ligustral Or Triplal | 0.547 |
| 54 | 115-95-7 | Linalyl Acetate | 1.193 |
| 55 | 106-72-9 | Melonal | 0.348 |
| 56 | 6413-10-1 | Methyl Dioxolan | 1.988 |
| 57 | 67674-46-8 | Methyl Pamplemousse | 0.199 |
| 58 | 93-92-5 | Methyl Phenyl Carbinyl Acetate | 0.199 |
| 59 | 111-79-5 | Methyl-2-Nonenoate | 0.050 |
| 60 | 7212-44-4 | Nerolidol | 0.298 |
| 61 | 59323-76-1 | Oxane | 0.030 |
| 62 | 5471-51-2 | Para Hydroxy Phenyl Butanone | 0.994 |
| 63 | 103-60-6 | Phenoxy Ethyl Iso Butyrate | 0.199 |
| 64 | 60-12-8 | Phenyl Ethyl Alcohol | 1.491 |
| 65 | 3658-77-3 | Pineapple Compound | 0.050 |
| 66 | 33885-51-7 | Pino Acetaldehyde | 0.050 |
| 67 | 52475-86-2 | Precyclemone B | 0.099 |
| 68 | 1191-16-8 | Prenyl Acetate | 0.298 |
| 69 | 78-69-3 | Tetra Hydro Linalool | 14.910 |
| 70 | 104-67-6 | Undecalactone | 0.696 |
| 71 | 81782-77-6 | Undecavertol | 0.298 |
| 72 | 88-41-5 | Verdox | 0.994 |
| 73 | | 1-butylsulfanylbutane | 0.003 |
| | 77-93-0 | Triethyl Citrate | 0.297 |
| 74 | | 5-mercapto-5 methyl-3-hexanone | 0.174 |
| 75 | 68398-18-5 | 4,7,7-trimethyl-6-thiabicyclo [3.2.1]octane | 0.120 |
| 76 | | Methoxyisobutylpyrazine monopropylene glycol | 0.000006 0.005994 |
| | | TOTALS : | 100.000 |

Optional Ingredients

The composition of the present invention may contain a fragrance modulator. Fragrance modulators enhance intensity of a fragrance profile over time, preferably so that the volatile fragrance materials remain significantly consistent from its initial impression to the end. Fragrance modulators are disclosed in U.S. Provisional Patent Ser. No. 61/915,514 which is incorporated by reference. Thus, in one aspect, said perfume composition comprises at least one non-odorous fragrance modulator formed of an alkoxylated methyl glucoside selected from the group consisting of methyl glucoside polyol, ethyl glucoside polyol, and propyl glucoside polyol, preferably PPG-20 Methyl Glucose Ether, in an amount from about 0.1 wt % to about 20 wt %, preferably about 0.5 wt % to about 18 wt %, or more preferably about 2.5 wt % to about 15 %, relative to the total weight of the composition.

In one aspect, the freshening composition comprises at least one low volatile PRM known in the art having a vapor pressure <0.001 Torr at 25° C., in the amount of from about 0.1 wt % to about 30 wt %, relative to the total weight of the perfume blend; and at least one volatile PRM known in the art having a vapor pressure ≥0.001 Torr 25° C. in the amount of from about 70 wt % to about 99.9 wt %, relative to the total weight of the perfume blend.

In another aspect, the freshening composition may comprise functional perfume components ("FPCs"). FPCs are a class of perfume raw materials with evaporation properties that are similar to traditional organic solvents or volatile organic compounds ("VOCs") commonly used in air freshening compositions. "VOCs" as used herein means volatile organic compounds that have a vapor pressure of greater than 0.2 mm Hg measured at 20° C. and aid in perfume evaporation. FPCs aid in the evaporation of perfume raw materials. In some embodiments, FPCs may provide a secondary fragrance benefit. In such embodiments, at least one perfume raw material that is not a FPC will be present to provide the hedonic benefits of the composition. FPCs may be used in relatively large concentrations without negatively impacting perfume character of the composition. Exemplary FPCs are disclosed in U.S. Pat. No. 8,338,346 and U.S. Pat. No. 8,637,446.

The freshening composition may comprise ethanol in the amount of from about 5 wt % to about 20 wt %, or from about 5 wt % to about 10 wt %, relative to the total weight of the freshening composition.

Freshening compositions can also incorporate desirable scents through inclusion of perfume blends in perfume delivery systems. Certain perfume delivery systems, methods of making certain perfume delivery systems, and the uses of such perfume delivery systems are disclosed in U.S. Publication No. 2007/0275866 A1. The perfumes blends and PRMs previously disclosed can be used in such perfume delivery systems. Such perfume delivery systems include: polymer-assisted delivery, molecule-assisted delivery, fiber-assisted deliver, amine-assisted delivery, cyclodextrin delivery system, starch encapsulated accord, inorganic carrier delivery system, and Pro-Perfume.

Suitable additional materials include, but are not limited to, malodor reducing actives (e.g. cyclodextrins, polyamine polymers (e.g. Lupasol™ polymers)), antimicrobials, surfactants, builders, chelating agents, dispersants, enzymes, and enzyme stabilizers, catalytic materials, polymeric dispersing agents, carriers, and/or pigments known in the art.

For the purposes of the present invention, the non-limiting list of adjuncts illustrated hereinafter are suitable for use in the instant compositions and may be desirably incorporated in certain aspects of the invention, for example, to assist or enhance performance or to modify the aesthetics of the composition. It is understood that such adjuncts are in addition to the components that are supplied via Applicants' perfume blends. The precise nature of these additional components, and levels of incorporation thereof, will depend on the physical form of the composition and the nature of the operation for which it is to be used.

Air Care Product

As the freshening compositions disclosed herein are anti-habituating, such compositions may be used without resorting to switching/alternating the composition, as is common in air care devices, so the consumer does not become habituated. The present invention includes an apparatus for the delivery of a volatile material to the atmosphere or an air care product. It is contemplated that the apparatus may be configured for use in a variety of applications to deliver volatile materials to the atmosphere.

For example, the apparatus may be configured for use with an energized device. An exemplary energized device may be an electrical heating device. More particularly, the device may be an electrical wall plug air freshener as described in U.S. Pat. No. 7,223,361; a battery powered heating device; or other heating devices (e.g. devices powered by chemical reactions such as catalyst fuel systems; solar powered devices, etc.). In such devices, the volatile material delivery engine may be placed next to the heating surface to diffuse the volatile perfume material. The volatile perfume material formula may be adjusted to include an overall lower vapor pressure formula. An exemplary perfume blend with a suirable blend of vapor pressure ranges is shown in Table 4.

TABLE 4

| Wt % of PRMs | Average VP @ 25° C., (torr) | Lo VP @ 25° C., (torr) | Hi VP @ 25° C., (torr) |
|---|---|---|---|
| 8.00 | 1.00E−01 | 1.13E−01 | and up |
| 10.00 | 7.50E−02 | 8.75E−02 | 6.25E−02 |
| 12.00 | 5.00E−02 | 6.25E−02 | 3.75E−02 |
| 17.00 | 2.50E−02 | 3.25E−02 | 1.75E−02 |
| 19.00 | 1.00E−02 | 1.13E−02 | 8.75E−03 |
| 17.00 | 7.50E−03 | 8.75E−03 | 6.25E−03 |
| 11.00 | 5.00E−03 | 6.25E−03 | 3.75E−03 |
| 5.00 | 2.50E−03 | and below | 1.75E−03 |

The apparatus may also be configured for use with an air purifying system to deliver both purified air and volatile materials to the atmosphere. Non-limiting examples include air purifying systems using ionization and/or filtration technology for use in small spaces (e.g. bedrooms, bathrooms, automobiles, etc.), and whole house central air conditioning/heating systems (e.g. HVAC).

The apparatus may also be configured for use with an aerosol or non-aerosol air spray. In this embodiment, the delivery engine can deliver volatile materials upon user demand or programmed to automatically deliver volatile materials to the atmosphere.

The apparatus may also be configured for use with a fan to deliver volatile materials to the atmosphere.

In one aspect, an apparatus for delivering a volatile material comprising a delivery engine having a liquid reservoir for containing a volatile material and a breathable membrane enclosing the liquid reservoir as disclosed in U.S. Pat. No. 8,709,337 and U.S. Pat. No. 8,931,711.

Method of Use and Use

Certain air care products disclosed herein can be used to impart anti-habituation properties to a perfume and/or air care product that results in an improved freshness over time of such perfume and/or consumer is disclosed.

In one aspect, the use of one or more sulfur-containing PRMs disclosed herein to impart anti-habituation properties to a freshening composition and/or air care product that results in an improved freshness over time of such perfume and/or consumer, wherein such PRMs are selected from the group consisting of sulfur-containing PRMs as disclosed herein.

In one aspect, a method for producing an air care product comprising bringing into contact or mixing into the product an organoleptically active quantity of a sulfur accord disclosed herein.

TEST METHODS

The degree of habituation to a freshening composition containing a sulfur-containing PRM is determined via human panel testing with daily exposures to the scent over a four week period, and is calculated at both the week two and week four time points, relative to the initial baseline time point.

For each exposure panel test, more than 15 panelists are recruited. The panelists are exposed to the test scent in a manner, frequency, and concentration indicated by the intended product end use, but including at least one exposure per day every day for four consecutive weeks. The perfume exposure must be sufficient that the panelists can detect the perfume of interest being delivered from the product or perfume delivery system contained within the product. The criteria for recruitment onto the exposure panel requires that panelists be typical consumers of the product in question, who agree to use the scent being tested, are non-smokers, and free of nasal congestion and allergies. The degree of habituation is calculated and reported as the percent change in the Odor Detection Threshold ("ODT") value at week two and at week four, versus the initial baseline ODT value. Since the degree of habituation is a relative measure, it accommodates the variation in absolute ODT values which can arise between different testing laboratories.

Raw materials and finished products comprising them may be used together in conjunction in order to determine the degree of habituation. For example, daily exposures to the panelists may involve the use of a finished product while the ODT test measurements may involve the use of the respective neat perfume or PRM. The conditions selected for use in either the daily exposures or in the ODT testing must be applied uniformly across all panelists, and remain unchanged for the entirety of the four week testing period. When the test perfume materials are available in their simple forms i.e., PRM, neat perfume, or fine fragrance, unincorporated into complex products or delivery systems, then the ODT test is to be conducted with these simple forms via an olfactometer, as this is the preferred method. When these simple forms of the test perfume materials are inaccessible for testing, then the ODT test may be conducted with finished products or complex formulations comprising the test perfume materials. Presentation devices other than an olfactometer may be required when conducting the ODT testing on finished products or complex formulations, and may include devices such as sniff cups, headspace chambers and capped bottles, as allowed for in the test method ASTM E679-04 described below.

The ODT value for each panelist is determined at each of three time points the during four week daily exposure period, namely; at initial baseline, at two weeks, and at four weeks. The ODT values are always to be determined in accordance with test method ASTM E679-04 (Standard Practice for Determination of Odor and Taste Thresholds by a Forced-Choice Ascending Concentration Series of Limits) as reapproved in 2011 except, the following replaces the protocol of such test method's Sub-articles 4.4, 8.2 and 8.3.

Sub-article 4.4, Individual best-estimate values of the threshold are derived from the pattern of correct/incorrect responses produced separately by each panelist. The group average ODT value at a given time point is derived by fitting the entire data set from all panelists at that time point to a Log Logistic Regression Model.

Sub-article 8.2, If the concentration range has been correctly selected, it is not necessary that all panelists judge correctly within the range of concentration steps provided. Thus, the representation of the panelists' judgments as in 8.1 need not terminate with two or more consecutive plusses (+).

Sub-article 8.3, Since there is a finite probability that a correct answer will occur by chance alone, it is important that a panelist repeat the test three times. Panelists who fail the test at the highest concentration, are deemed anosmic to the test material and their response is removed from the data set.

Additionally, the following selections are made in accordance with the test method's sub-articles 1.3, 1.4, 1.6, 1.7, and 4.1, and specified here as per sub-article 9.3.

Sub-article 1.3, The threshold is characterized as being a) only detection (awareness) that a very small amount of added substance is present but not necessarily recognizable.

Sub-article 1.4, When the preferred method is being conducted, namely using a simple perfume form presented via olfactometer, then the presentation medium can be an air, pure nitrogen, or a mixture of the two. When testing finished or complex products, alternative presentation media may be used, such as air.

Sub-article 1.6, When the preferred method is being conducted, namely using a simple perfume form presented via olfactometer, then the physical method of presentation is at a rate of 40 L/min. When testing finished or complex products, alternative presentation devices may be used, including but not limited to sniff cups, headspace chambers or capped bottles.

Sub-article 1.7, Presentation is made to a panel of greater than 15 panelists, who are participating in the daily exposure panel.

Sub-article 4.1, Eight scale steps are used, with each step having an individual predetermined dilution factor suitable for the stimuli being tested, at a temperature of 35° C. PRM or neat perfume stimuli are typically introduced to the olfactometer system in the neat form via a pump syringe. Sometimes a dilution of the stimuli with ethanol is needed.

The group average ODT values from the three time points are used to calculate the degree of habituation. The degree of habituation is reported for 2 specific time points, as the percent change in group average ODT at one time point, relative to the group average ODT at the initial baseline time point. The degree of habituation is determined at the time points of: 2 weeks and 4 weeks, of the four week daily exposure period, using the following formula:

$$\text{Degree of Habituation (percent change in ODT) at Time } X = ((\text{Group Average ODT}_{Time\ X} - \text{Group Average ODT}_{Baseline})/\text{Group Average ODT}_{Baseline}) \times 100$$

where Time X is either 2 weeks, or 4 weeks, of repeated daily exposure.

A perfume is considered to have an anti-habituation index of:

For a two week test:
Zero (0) when the Degree of Habituation after 2 weeks of exposure to said perfume is from about 150% to 25%
One (1) when the Degree of Habituation after 2 weeks of exposure to said perfume is less than 25% but greater than 10%;
Two (2) when the Degree of Habituation after 2 weeks of exposure to said perfume is from 10% to 0%; or Three (3) when the Degree of Habituation after 2 weeks of exposure to said perfume is less than 0% to about −25%.

Four (4) when the Degree of Habituation after 2 weeks of exposure to said perfume is less than −25% to about −500%

For a four week test:

Zero (0) when the Degree of Habituation after 4 weeks of exposure to said perfume is from about 150% to 25%

One (1) when the Degree of Habituation after 4 weeks of exposure to said perfume is less than 25% but greater than 10%;

Two (2) when the Degree of Habituation after 4 weeks of exposure to said perfume is from 10% to 0%; or Three (3) when the Degree of Habituation after 4 weeks of exposure to said perfume is less than 0% to about −25%.

Four (4) when the Degree of Habituation after 4 weeks of exposure to said perfume is less than −25% to about −500%

EXAMPLES

Approximately 135 test subjects per usage group were recruited for the study. The test subjects placed in the study were assessed for their baseline threshold intensity according to the ODT method defined above for the perfume of interest that was in the product. Test subjects were placed into four test legs (30-35 test subjects per leg). Two legs had compositions with the sulfur accord and two legs had composition without the sulfur accord as shown in Table 5.

The freshening compositions are prepared by mixing all of the PRMs and stiffing for approximately 30 minutes in a suitable vessel. The 30 minute interval should be sufficient to achieve a homogenous solution.

TABLE 5

| Composition | Description | Wt % of sulfur-containing PRMs in perfume blend |
|---|---|---|
| 1 | Perfume Blend having sulfur accord of Table 6 | 0.076 |
| 2 | Perfume Blend having sulfur accord of Table 7 | 0.297 |
| 3 | Perfume Blend having oxane | 0.015 |
| 4 | Perfume Blend having 0.01% of 8-mercaptomenthone and 0.000001% of 4-mercapto-4-methylpentan-2-one | 0.010 |

TABLE 6

Composition 1 Sulfur Accord

| PRM | wt % in Composition | wt % in sulfur accord of |
|---|---|---|
| 2-Isobutylthiazole (CAS#18640-74-9) | 0.0055 | 7.2430368 |
| 2-Isopropyl-4-methyl thiazole | 0.0055 | 7.2430368 |
| 4-methyl-5-thiazoleethanol (2-(4-methyl-1,3-thiazol-5-yl)ethanol) (CAS#137-00-8) | 0.0550 | 72.430368 |
| 8-mercaptomenthone | 0.009934 | 13.08224 |
| 4-mercapto-4-methylpentan-2-one | 0.0000009934 | 0.00001308224 |
| TOTAL | 0.075935 | 100.000 |

TABLE 7

Composition 2 Sulfur Accord

| PRMs | wt % in composition | wt % of in sulfur accord |
|---|---|---|
| 1-butylsulfanylbutane | 0.003 | 1.010 |
| 5-mercapto-5-methyl-3-hexanone | 0.174 | 58.586 |
| 4,7,7-trimethyl-6-thiabicyclo[3.2.1]octane | 0.120 | 40.404 |
| TOTAL | 0.297 | 100.000 |

The four study groups with a freshenining composition according to Compositions 1-4 and instructed to use a Febreze NOTICEables air care product with the respective Composition (1, 2, 3, or 4) as they normally would use their current air care product throughout the four week study period, using no other air care products throughout the duration of the study. Their ODT was measured after 4 weeks of usage. The average ODT was calculated for each usage group. Results are shown in Table 8. Additionally, all test subjects completed standard after-use questionnaires after 2 and 4 weeks of product usage to obtain their feedback and assess key product attributes.

TABLE 8

| | Composition 1 | Composition 2 | Composition 3 | Composition 4 |
|---|---|---|---|---|
| Degree of Habituation* (after 4 weeks) | −79.25* | −67.76* | 491.86* | −27.92* |
| Overall Rating (after 4 weeks) | 60 | 73 | 54 | 60 |

*Higher values equate to more habituation

The results in Table 8 show that the inclusion of 1-butylsulfanylbutane in the sulfur accord (i.e. Composition 2) has anti-habituating effects vs. the control without 1-butylsulfanylbutane (i.e. Composition 2 driving a higher overall rating score after 4 weeks (73 vs. 60 and 54).

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

What is claimed is:

1. A freshening composition comprising a perfume blend comprising about 0.0000001% to about 10%, by weight of said perfume blend, of a sulfur accord, said sulfur accord comprises:
  (a) about 1% to about 99%, by weight of said sulfur accord, of 1-butylsulfanylbutane; and
  (b) about 1% to about 99%, by weight of said sulfur accord, of a sulfur-containing perfume raw material selected from the group consisting of: 2-(4-methyl-1,3-thiazol-5-yl)ethanol; 2-methylthio-3-methyl sulfanyl pryazine; 5-Mercapto-5-methyl-3-hexanone; 4,7,7-trimethyl-6-thiabicyclo[3.2.1]octane; 2-isobutylthiazole; 2-isopropyl-4-methyl thiazole; 5-methyl-2-(2-sulfanylpropan-2-yl)cyclohexan-1-one; limonene thiol; 4 methyl 4 mercapto pentane 2 one 1 ppm TEC; 2-acetyl thiazole; oxane; 4-methoxy-2-methyl-2-butanethiol; and mixtures thereof;
wherein said composition resists the fragrance habituation of a consumer to the freshening composition.

2. The composition of claim 1, wherein said sulfur accord further comprises a perfume raw material having a sulfide moiety selected from the group consisting of: ethyl 3-methylsulfanylpropanoate; 2-(methylsulfanylmethyl)furan; methylsulfanylmethane; methylsulfanylethane; 3-methylsulfanylprop-1-ene; S-methyl ethanethioate; ethylsulfanylethane; 1-methylsulfanylpropane; S-ethyl ethanethioate; 1-methylsulfanylbutane; 2-propan-2-ylsulfanylpropane; bis(methylsulfanyl)methane; 1-ethylsulfanylpropane; thiolane; 1-propylsulfanylpropane; 1-ethylsulfanylbutane; S-ethyl propanethioate; S-methyl butanethioate; S-methyl 3-methylbutanethioate; 3-methylsulfanylpropanal; 3-prop-2-enylsulfanylprop-1-ene; methyl 2-methylsulfanylacetate; S-prop-2-enyl propanethioate; 1-methylsulfanylbutan-2-one; 4-methylsulfanylbutan-2-one; 3-methylsulfanylpropan-1-am; 2,4,6-trimethyl-1,3,5-trithiane; 3-methylsulfanylbutanal; 2-methyl-1,3-thiazolidine; 2-methyl-4,5-dihydro-1,3-thiazole; ethyl 2-methylsulfanylacetate; methyl 3-methylsulfanylpropanoate; S-propan-2-yl 3-methylbutanethioate; 4-methyl-4-methylsulfanylpentan-2-one; 2-methyl-1,3-dithiolane; methyl 2-methylsulfanylbutanoate; S-methyl furan-2-carbothioate; S-propan-2-yl 3-methylbut-2-enethioate; thiolan-3-one; 3,5-diethyl-1,2,4-trithiolane; methylsulfanylmethylbenzene; 3-methylsulfanylpropan-1-ol; 2-(propan-2-ylsulfanylmethyl)furan; 2-methyl-5-methylsulfanylfuran; S-(furan-2-ylmethyl) methanethioate; 1,2,4-trithiolane; 2-methylthiolan-3-one; 4-methylsulfanylbutan-1-ol; S-butan-2-yl 3-methylbutanethioate; S-butan-2-yl 3-methylbut-2-enethioate; S-(furan-2-ylmethyl) ethanethioate; 2-propyl-1,3-thiazolidine; 3-methyl-1,1-bis(methylsulfanyl)butane; 3-ethylsulfanylpropan-1-ol; S-methyl benzenecarbothioate; 3,5-dimethyl-1,2,4-trithiolane; S-butan-2-yl 2-methylbutanethioate; methylsulfanylbenzene; 1-pentylsulfanylpentane; (2R,4S)-2-methyl-4-propyl-1,3-oxathiane; 2-methyl-4-propyl-1,3-oxathiane; ethyl 2-methyl-2-methylsulfanylpropanoate; S-(furan-2-ylmethyl) propanethioate; 4,7,7-trimethyl-6-thiabicyclo[3.2.1]octane; 3-methyl-1,2,4-trithiane; methylsulfanylmethyl hexanoate; 1-(4,5-dihydro-1,3-thiazol-2-yl)ethanone; 3-methylsulfanylpropanoic acid; 5-methylsulfanyl-2-(methylsulfanylmethyl)pent-2-enal; 4,5-dimethyl-2-(2-methylpropyl)-2,5-dihydro-1,3-thiazole; 3-methylsulfanylhexan-1-ol; 2-methyl-4,5-dihydrofuran-3-thiol acetate; 4-(3-oxobutylsulfanyl)butan-2-one; 3-methylsulfanylbutanoic acid; 2-methylsulfanylpyrazine; 2-methyl-3-methylsulfanylpyrazine; 2-(furan-2-ylmethylsulfanylmethyl)furan; 2-(methylsulfanylmethyl)pyrazine; 3,5-di(propan-2-yl)-1,2,4-trithiolane; 2-methylsulfanylphenol; 2-methyl-3-methylsulfanylpyrazine; ethyl 3-(furan-2-ylmethylsulfanyl)propanoate; 2,2,4,4,6,6-hexamethyl-1,3,5-trithiane; 2-methyl-5,7-dihydrothieno[3,4-d]pyrimidine; 2-amino-4-methylsulfanylbutanoic acid; (2S)-2-amino-4-methylsulfanylbutanoic acid; 2',3a-dimethylspiro[6,6a-dihydro-5H-[1,3]dithiolo[4,5-b]furan-2,3'-oxolane]; 2,5-dimethyl-1,4-dithiane-2,5-diol; Methyl 2-thiofuroate; and mixtures thereof.

3. The composition of claim 1, wherein said (b) sulfur-containing perfume raw material comprises:
  (i) 5-mercapto-5-methyl-3-hexanone or 4,7,7-trimethyl-6-thiabicyclo[3.2.1]octane; and
  (ii) a sulfur-containing raw material selected from the group consisting of: 2-(4-methyl-1,3-thiazol-5-yl)ethanol; 2-(2-methylpropyl)-1,3-thiazole; 4-methyl-2-propan-2-yl-1,3-thiazole; 5-methyl-2-(2-sulfanylpropan-2-yl)cyclohexan-1-one; 6-Thiabicyclo[3.2.1]octane; 4-methyl-4-sulfanylpentan-2-one; 8-Mercaptomenthone; (2R,4S)-2-methyl-4-propyl-1,3-oxathiane; and mixtures thereof.

4. The composition of claim 1, wherein said sulfur accord comprises 1-butylsulfanylbutane; 5-mercapto-5-methyl-3-hexanone; and 4,7,7-trimethyl-6-thiabicyclo[3.2.1]octane.

5. The composition of claim 1 wherein said 1-butylsulfanylbutane is present in an amount from about 0.003% to about 0.01%, by weight of said freshening composition.

6. The composition of claim 1 wherein said 1-butylsulfanylbutane is present in an amount of about 1% to about 10%, by weight of said sulfur accord.

7. The composition of claim 1 wherein said composition has:
  a two week anti-habituation index of 0, 1, 2, 3 or 4; and/or
  a four week anti-habituation index of 0, 1, 2, 3 or 4.

8. The composition of claim 1 further comprising a freshening material selected from the group consisting of perfume delivery systems, functional perfume components, malodor reducing actives, surfactants, and mixtures thereof.

9. The composition of claim 1, wherein said perfume blend comprises at least one low volatile fragrance material having a vapor pressure less than 0.001 Torr at 25C; and the low volatile fragrance material is present in an amount of from about 0.1 wt % to about 30 wt %, by weight of said perfume blend.

10. A freshening composition comprising a perfume blend, said perfume blend comprising about 0.0000001% to about 10%, by weight of said perfume blend, of a sulfur accord, said sulfur accord comprises from about 0.003% to about 0.01%, by weight of said composition, of 1-butylsulfanylbutane, 5-mercapto-5-methyl-3-hexanone, and 4,7,7-trimethyl-6-thiabicyclo[3.2.1]octane.

11. The composition of claim 10, wherein said 5-mercapto-5-methyl-3-hexanone is present in an amount from about 0.1% to about 0.2%, by weight of said composition.

12. The composition of claim 10, wherein said 4,7,7-trimethyl-6-thiabicyclo[3.2.1]octane is present in an amount from about 0.1% to about 0.2%, by weight of said composition.

13. The composition of claim 10, wherein said 1-butylsulfanylbutane is present in an amount of about 1% to about 10%, by weight of said sulfur accord.

14. The composition of claim 10, wherein said 5-mercapto-5-methyl-3-hexanone is present in an amount of about 40% to about 99%, by weight of said sulfur accord.

15. The composition of claim 10, wherein said 4,7,7-trimethyl-6-thiabicyclo[3.2.1]octane is present in an amount of about 40% to about 99%, by weight of said sulfur accord.

16. The composition of claim 10 further comprising a freshening material selected from the group consisting of perfume delivery systems, functional perfume components, malodor actives, surfactants, and mixtures thereof.

17. A method of reducing fragrance habituation comprising providing the composition of claim 1 or claim 10.

18. The composition of claim 1, wherein said sulfur accord comprises 1-butylsulfanylbutane and 2-methylthio-3-methyl sulfanyl pyrazine.

19. The composition of claim 1, wherein said sulfur accord comprises 1-butylsulfanylbutane and 5-Mercapto-5-methyl-3-hexanone.

20. The composition of claim 1, wherein said sulfur accord comprises 1-butylsulfanylbutane and 2-isobutylthiazole.

21. The composition of claim 1, wherein said sulfur accord comprises 1-butylsulfanylbutane and 2-isopropyl-4-methyl thiazole.

22. The composition of claim 1, wherein said sulfur accord comprises 1-butylsulfanylbutane and limonene thiol.

23. The composition of claim 1, wherein said sulfur accord comprises 1-butylsulfanylbutane and 4 methyl 4 mercapto pentane 2 one 1ppm TEC.

24. The composition of claim 1, wherein said sulfur accord comprises 1-butylsulfanylbutane and 2-acetyl thiazole.

25. The composition of claim 1, wherein said sulfur accord comprises 1-butylsulfanylbutane, 2-(4-methyl-1,3-thiazol-5-yl)ethanol, 2-methylthio-3-methyl sulfanyl pyrazine, and 2-acetyl thiazole.

26. The composition of claim 1, wherein said sulfur accord comprises 1-butylsulfanylbutane, 5-Mercapto-5-methyl-3-hexanone, 4,7,7-trimethyl-6-thiabicyclo[3.2.1]octane, and oxane.

27. The composition of claim 1, wherein said sulfur accord comprises 1-butylsulfanylbutane, 4,7,7-trimethyl-6-thiabicyclo[3.2.1]octane, limonene thiol, and oxane.

28. The composition of claim 1, wherein said sulfur accord comprises 1-butylsulfanylbutane, 2-isobutylthiazole, 2-isopropyl-4-methyl thiazole, and 4 methyl 4 mercapto pentane 2 one 1ppm TEC.

29. The composition of claim 1, wherein said sulfur accord comprises 1-butylsulfanylbutane, 5-methyl-2-(2-sulfanylpropan-2-yl)cyclohexan-1-one, oxane, and 4-methoxy-2-methyl-2-butanethiol.

30. The composition of claim 1, wherein said sulfur accord comprises 1-butylsulfanylbutane, 2-methylthio-3-methyl sulfanyl pyrazine, and 5-Mercapto-5-methyl-3-hexanone.

31. The composition of claim 1, wherein said sulfur accord comprises 1-butylsulfanylbutane, 2-(4-methyl-1,3-thiazol-5-yl)ethanol, and 2-acetyl thiazole.

32. The composition of and of claim 1, wherein said sulfur accord comprises 1-butylsulfanylbutane, 5-Mercapto-5-methyl-3-hexanone, 4,7,7-trimethyl-6-thiabicyclo[3.2.1]octane, and limonene thiol.

33. The composition of and of claim 1, wherein said sulfur accord comprises 1-butylsulfanylbutane, 2-(4-methyl-1,3-thiazol-5-yl)ethanol, and 2-methylthio-3-methyl sulfanyl pyrazine.

34. The composition of and of claim 1, wherein said sulfur accord comprises 1-butylsulfanylbutane, 4,7,7-trimethyl-6-thiabicyclo[3.2.1]octane, and limonene thiol.

35. The composition of and of claim 1, wherein said sulfur accord comprises 1-butylsulfanylbutane, 4,7,7-trimethyl-6-thiabicyclo[3.2.1]octane, 5-methyl-2-(2-sulfanylpropan-2-yl)cyclohexan-1-one, and 4-methoxy-2-methyl-2-butanethiol.

36. The composition of and of claim 1, wherein said sulfur accord comprises 1-butylsulfanylbutane, 4,7,7-trimethyl-6-thiabicyclo[3.2.1]octane, 5-methyl-2-(2-sulfanylpropan-2-yl)cyclohexan-1-one, and limonene thiol.

37. The composition of claim 1, wherein said sulfur accord comprises 1-butylsulfanylbutane, 5-methyl-2-(2-sulfanylpropan-2-yl)cyclohexan-1-one, limonene thiol, and 4-methoxy-2-methyl-2-butanethiol.

38. The composition of claim 1, wherein said sulfur accord comprises 1-butylsulfanylbutane, 2-isobutylthiazole, 2-isopropyl-4-methyl thiazole, and 4 methyl 4 mercapto pentane 2 one 1ppm TEC.

39. The composition of and of claim 1, wherein said sulfur accord comprises 1-butylsulfanylbutane, 2-(4-methyl-1,3-thiazol-5-yl)ethanol, 2-isopropyl-4-methyl thiazole, and 4 methyl 4 mercapto pentane 2 one 1ppm TEC.

40. The composition of and of claim 1, wherein said sulfur accord comprises 1-butylsulfanylbutane, 2-(4-methyl-1,3-thiazol-5-yl)ethanol 2-isobutylthiazole, and 2-isopropyl-4-methyl thiazole.

41. The composition of and of claim 1, wherein said sulfur accord comprises 1-butylsulfanylbutane, 5-methyl-2-(2-sulfanylpropan-2-yl)cyclohexan-1-one, 4 methyl 4 mercapto pentane 2 one 1ppm TEC, and 4-methoxy-2-methyl-2-butanethiol.

42. The composition of and of claim 1, wherein said sulfur accord comprises 1-butylsulfanylbutane, 5-Mercapto-5-methyl-3-hexanone; 4,7,7-trimethyl-6-thiabicyclo[3.2.1]octane, and 4-methoxy-2-methyl-2-butanethiol.

* * * * *